(12) United States Patent
Dorn et al.

(10) Patent No.: US 7,358,343 B2
(45) Date of Patent: *Apr. 15, 2008

(54) ENDOHEDRAL METALLOFULLERENE DERIVATIVES

(75) Inventors: Harry C. Dorn, Blacksburg, VA (US); Erick B. Iezzi, Blacksburg, VA (US); James Duchamp, Emory, VA (US)

(73) Assignee: Virginia Tech Intellectual Properties, Inc., Blacksburg, VA (US)

(*) Notice: Subject to any disclaimer, the term of this patent is extended or adjusted under 35 U.S.C. 154(b) by 103 days.

This patent is subject to a terminal disclaimer.

(21) Appl. No.: 10/244,747

(22) Filed: Sep. 17, 2002

(65) Prior Publication Data
US 2004/0054151 A1 Mar. 18, 2004

(51) Int. Cl.
*C07F 5/00* (2006.01)
(52) U.S. Cl. .............. 534/15; 424/1.11; 424/1.65; 556/1; 556/28

(58) Field of Classification Search .................... 534/7, 534/10–16; 556/1, 28; 505/460; 423/445 B
See application file for complete search history.

(56) References Cited

U.S. PATENT DOCUMENTS 6,303,760 B1 * 10/2001 Dorn et al. .................... 534/11

* cited by examiner

*Primary Examiner*—Dameron L. Jones
(74) *Attorney, Agent, or Firm*—Whitham Curtis Christofferson & Cook, PC

(57) ABSTRACT

Trimetallic nitride endohedral metallofullerene derivatives and their preparation are described. The trimetallic nitride endohedral metallofullerene derivatives have the general formula $A_{3-n}X_n@C_m(R)$ where n ranges from 0 to 3, A and X may be trivalent metals and may be either rare earth metal or group IIIB metals, m is between about 60 and about 200, and R is preferably an organic group. Derivatives where the R group forms cyclized derivatives with the fullerene cage are also described.

24 Claims, 3 Drawing Sheets a)

b)

ENDOHEDRAL METALLOFULLERENE DERIVATIVES

This invention was made with Government support under contract NCC-1-01044 awarded by NASA. The Government has certain rights in this invention.

FIELD OF THE INVENTION

The present invention is directed to derivatives of endohedral metallofullerenes. More particularly, the present invention is directed to derivatives of trimetallic nitride endohedral metallofullerenes.

BACKGROUND OF THE INVENTION

Fullerenes are a family of closed-caged molecules made up of carbon atoms. The closed-caged molecules consist of a series of five and six member carbon rings. The fullerene molecules can contain 500 or more carbon atoms. The most common fullerene is the spherical $C_{60}$ molecule taking on the familiar shape of a soccer ball.

Fullerenes are typically produced by an arc discharge method using a carbon rod as one or both of the electrodes in a Krätschmer-Huffman generator. Krätschmer, W. et al., Chem. Phys. Lett., 170, 167-170 (1990) herein incorporated by reference in its entirety. Typically, the generator has a reaction chamber and two electrodes. The reaction chamber is evacuated and an inert gas is introduced in the reaction chamber at a controlled pressure. A potential is applied between the electrodes in the chamber to produce an arc discharge. The arc discharge forms a carbon plasma in which fullerenes of various sizes are produced.

Over the past decade, derivatives of the empty-cage $C_{60}$ fullerene by organic functionalization chemistry has grown exponentially since the molecule was discovered to possess reactive double bonds at the [6,6] ring junctures of the cage, otherwise known as pyracyclene type units. Each $C_{60}$ molecular cage contains six of these reactive units; however, the [6,6] junctures of larger empty cages like $C_{70}$ and $C_{78}$ are not as reactive as $C_{60}$.

U.S. Pat. No. 6,303,760, herein incorporated by reference in its entirety, describes a family of endohedral metallofullerenes where a trimetallic nitride is encapsulated in a fullerene cage. The endohedral metallofullerenes have the general formula $A_{3-n}X_nN@C_m$ (n=0-3) where A is a metal, X is a second trivalent metal, n is an integer from 0 to 3, and m is an even integer from about 60 to about 200. The metals A and X may be an element selected from the group consisting of a rare earth element and a group IIIB element and may be the same or different. In some embodiments, A and X may be selected from the group consisting of Scandium, Yttrium, Lanthanum, Gadolinium, Holmium, Erbium, Thulium, and Ytterbium, where A and X may be the same or different. These novel trimetallic nitride endohedral metallofullerenes are produced by introducing nitrogen gas into the Krätschmer-Huffman generator during vaporization of packed graphite rods containing corresponding metal oxides, known as the trimetallic nitride template (TNT) process.

Although novel derivatives of empty cages have been synthesized by organic functionalization chemistry, derivatives of endohedral metallofullerenes have not yet been produced. Derivatization of empty-cage fullerenes such as $C_{60}$ occurs at highly reactive sites at a [6,6] ring junction of a pyracyclene-type units. These pyracyclene-type units are constructed of two fused hexagons abutted by neighboring pentagons. FIG. 1a illustrates the pyracyclene-type unit of a $C_{60}$ fullerene cage. However, some larger fullerenes, such as $C_{80}$, do not possess these reactive sites. Derivatives of endohedral metallofullerenes have the potential to provide the ability to create unique molecules with extraordinary properties due to the wide variety of metals and metal clusters that can be encapsulated inside the carbon cages of endohedral metallofullerenes. Accordingly, it is highly desirable to produce derivatives of these endohedral metallofullerenes.

SUMMARY OF THE INVENTION

The present invention is directed to a family of endohedral metallofullerenes derivatives having the formula $A_{3-n}X_nN@C_m(R)$ (n=0-3).

DESCRIPTION OF THE PREFERRED EMBODIMENTS

The present invention is directed to derivatives of trimetallic nitride endohedral metallofullerenes. In accordance with an embodiment of the present invention, trimetallic nitride endohedral metallofullerenes may be derivatized on the exterior of the fullerene cage with an organic group via cycloaddition reactions.

As used herein, "endohedral" refers to the encapsulation of atoms inside the fullerene cage network. Accepted symbols for elements and subscripts to denote numbers of elements are used herein. Further, all elements to the right of an @ symbol are part of the fullerene cage network, while all elements listed to the left are contained within the fullerene cage network. Under this notation, $Sc_3N@C_{80}(R)$ indicates that the $Sc_3N$ trimetallic nitride is situated within a $C_{80}$ fullerene cage and the R group is situated on the exterior of the $C_{80}$ fullerene cage and bonded to carbon of the fullerene cage.

The present invention is directed to a family of derivatized endohedral metallofullerenes represented generally as $A_{3-n}X_nN@C_m(R)$ (n=0-3) where A and X are metal atoms encapsulated in a fullerene cage and R is a group bonded to exterior of the fullerene cage.

Figure 1:
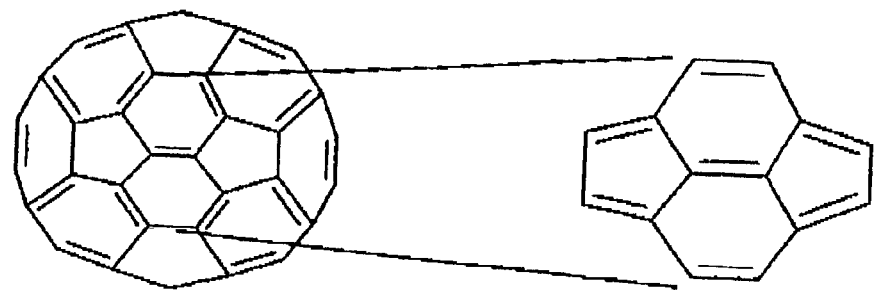
FIG. 1 shows a) an expansion of a [6,6] reactive site of a pyracyclene-type unit on a $C_{60}$ fullerene; and b) cage an expansion of [5,6] reacitve sites of a corannulene-type unit on a $C_{80}$ fullerene cage.
Figure 1:
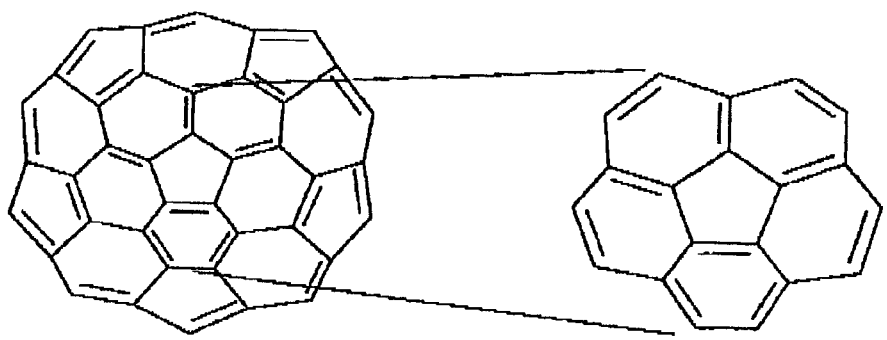

In accordance with the present invention, the fullerene cage, $C_m$, can range from about 68 carbon atoms to about 200 carbon atoms. In preferred embodiments, m can be about 68, about 78, or about 80. In one embodiment, the fullerene cage has a portion of the cage that corresponds to a corannulene-type unit. The corannulene-type unit consists of a five-member ring surrounded by five, six-member rings forming a five-member ring and six-member ring juncture, also called a [5,6] ring juncture. This configuration is illustrated in FIG. 1b, where the portion of the carbon cage has been expanded to illustrate the corannulene-type unit and the [5,6] ring junctures.

Figure 2:
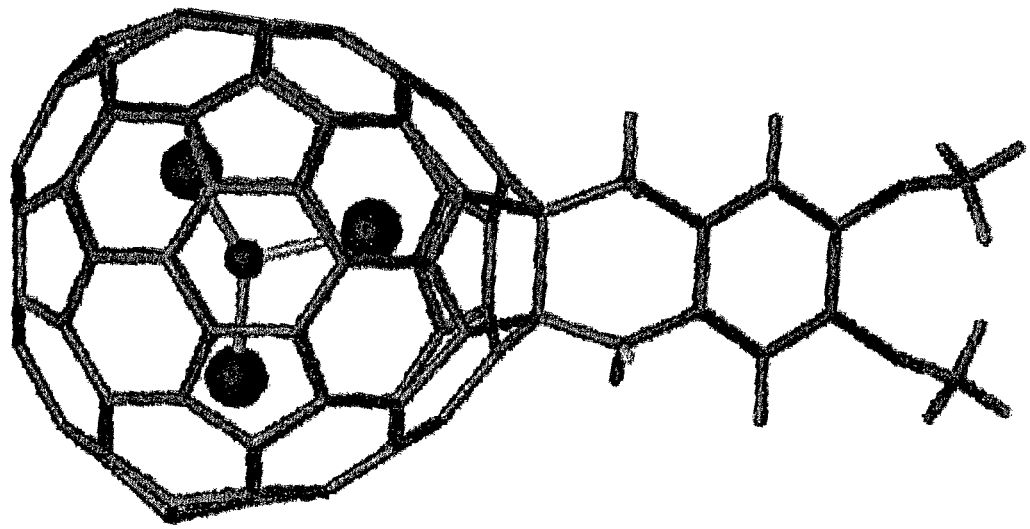
FIG. 2 illustrates the structure of $Sc_3N@C_{80}(C_{10}H_{12}O_2)$.

The R group is preferably an organic group positioned on the exterior of the fullerene cage. In one embodiment, the R group is associated with the carbon cage of the metallofullerene through at least two carbon atoms on the carbon cage. As shown in FIG. 2, the R group may form a cyclized derivative with the fullerene cage, where at least two carbons on the fullerene cage are part of the cyclized derivative. Preferably, the R group forms five or six-member rings with two carbon atoms on the fullerene cage. In a preferred embodiment, the R group is bonded to the fullerene cage through at least two carbon atoms on the corranulene-type unit. In some embodiments, the R group is bonded to the fullerene cage through a [5,6] ring juncture of the corranulene-type unit. In one embodiment, a single Diels-Alder addition product is formed on the cage of the endohedral metallofullerene.

In the case of a $C_{80}$ endohedral metallofullerene, without intending to be bound by theory, it is believed that the R group is formed on the metallofullerene cage through the cycloaddition of an organic group across the 1,2 position on the five-membered ring at a [5,6] ring juncture of a corannulene-type unit. By way of example, FIG. 2 illustrates a cycloaddition derivative of an organic group at the [5,6] ring juncture of a corannulene-type unit for $Sc_3N@C_{80}$ ($C_{10}H_{12}O_2$).

The type of R group is not particularly limited. In one embodiment, the R group is composed of carbon and hydrogen, and may include nitrogen as well as oxygen. Preferably, the R group has at least 3 carbon atoms. The R group may vary widely depending upon the desired properties of the metallofullerene derivative. For example, the R group may contain carboxyl or hydroxy groups to increase the water solubility of the derivative. Similarly, the hydrophilicity or hydrophobicity of the derivative may adjusted by varying the R group and its associated functional groups.

As discussed above, the [5,6] ring juncture in the corranulene-type unit of the metallofullerene is a reactive site. This site is reactive with respect to cycloaddition reactions. Virtually any compound that is expected to undergo cycloaddition reactions with π electrons can be used in accordance with the present invention to form the R group on the exterior of the fullerene cage. For instance, compounds that have an associated conjugated diene that are expected to undergo [4+2] cycloaddition may used. Further, the decarboxylation reaction of an amino acid and formaldehyde can be used to form a pyrrolidine derivative through 1,3-dipolar cycloaddition. Compounds that undergo [4+2], [3+2], (3,1-dipolar), [2+2] and [2+1] (Bingel reaction) cycloadditions as well as nucleophilic, electrophilic and radical additions may be used to form the R group on the fullerene cage. Some families of compounds that undergo cycloaddition include, but are not limited to, benzyne derivatives, ketenes, orthoquinodimethane derivatives, pyrrolidines, ylides, carbenes and malonate derivatives.

The encapsulated metals A and X may vary widely. Preferably, when the metallofullerene cage size is between about 68 carbon atoms and about 80 carbon atoms, the metal atoms are trivalent and have an ionic radius below about 0.095 nm. When the size of the fullerene cage is about 68, the metal atoms preferably have an ionic radius below about 0.090 nm for the $A_3N$ endohedral species. As the size of the cage increases, the ionic radius for the metal may increase. Further, A and X may be a rare earth element, a group IIIB element, or combinations thereof. Preferably, A and X may be Scandium, Yttrium, Lanthanum, Gadolinium, Holmium, Erbium, Thulium, Ytterbium, or other metals, and combination thereof.

To form the derivatives of the trimetallic endohedral metallofullerene, the desired trimetallic endohedral metallofullerene is reacted with the appropriate compound to form the organic R group on the fullerene cage. The preparation of trimetallic endohedral metallofullerenes is discussed in detail in U.S. Pat. No. 6,303,760, herein incorporated by reference in its entirety. Without intending to be bound by theory, it is believed that the reaction proceeds through a cycloaddition reaction between the desired trimetallic endohedral metallofullerene and the appropriate compound. Compounds that lend themselves to organic cycloaddition reactions, also called cycloaddition reagents, may be used with the present invention.

One skilled in the art will understand that solvents and reaction conditions for cycloaddition can vary depending upon the trimetallic endohedral metallofullerene and the cycloaddition reagent being used. In general, the cycloaddition reagent may be added to the trimetallic endohedral metallofullerene in the presence of a solvent, such as 1,2,4-trichlorobenzene, and refluxed for a sufficient time to form a derivative of the trimetallic endohedral metallofullerene. The reaction time will vary depending upon the reagents and solvent being used. One can use basic chemistry techniques, such as liquid chromatography, to monitor the reaction progress to determine when the reaction has completed.

The present invention is illustrated in the following examples. The examples are provided for illustration purposes and should not be construed as limiting the scope of the present invention.

EXAMPLE 1

Preparation of $Sc_3N@C_{80}(C_{10}H_{12}O_2)$

Figure 3:
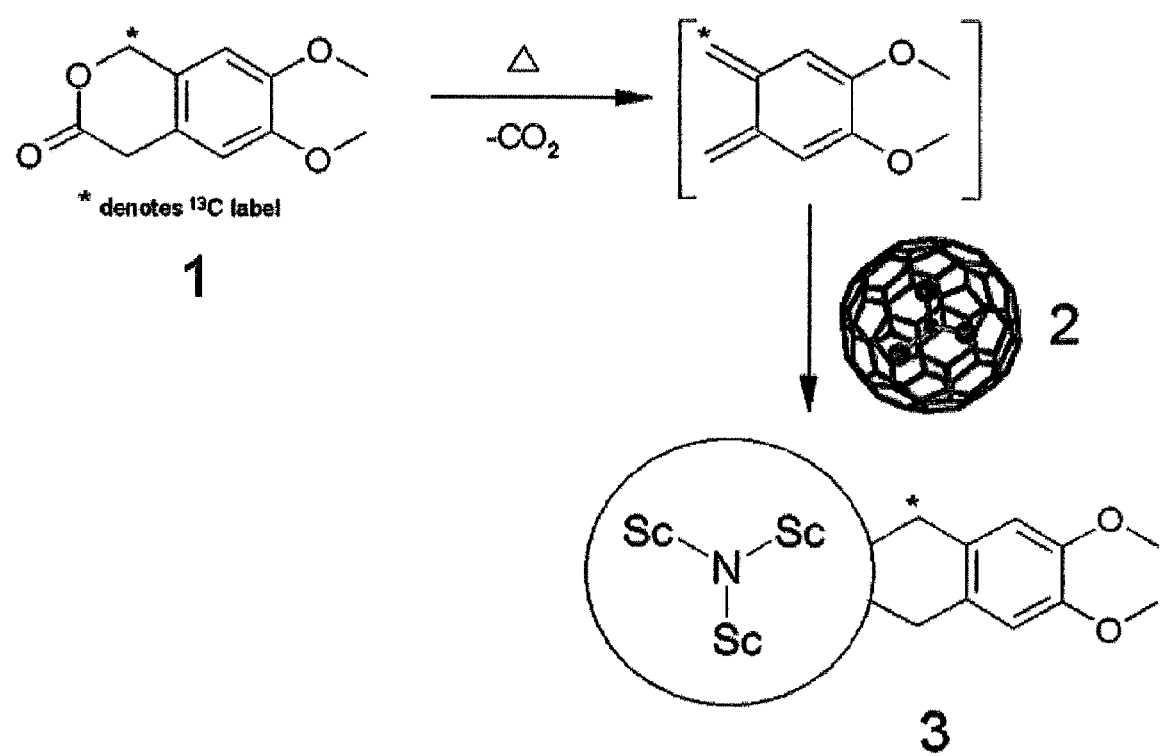
FIG. 3 illustrates the reaction scheme for the preparation of $Sc_3N@C_{80}(C_{10}H_{12}O_2)$.
Figure 4:
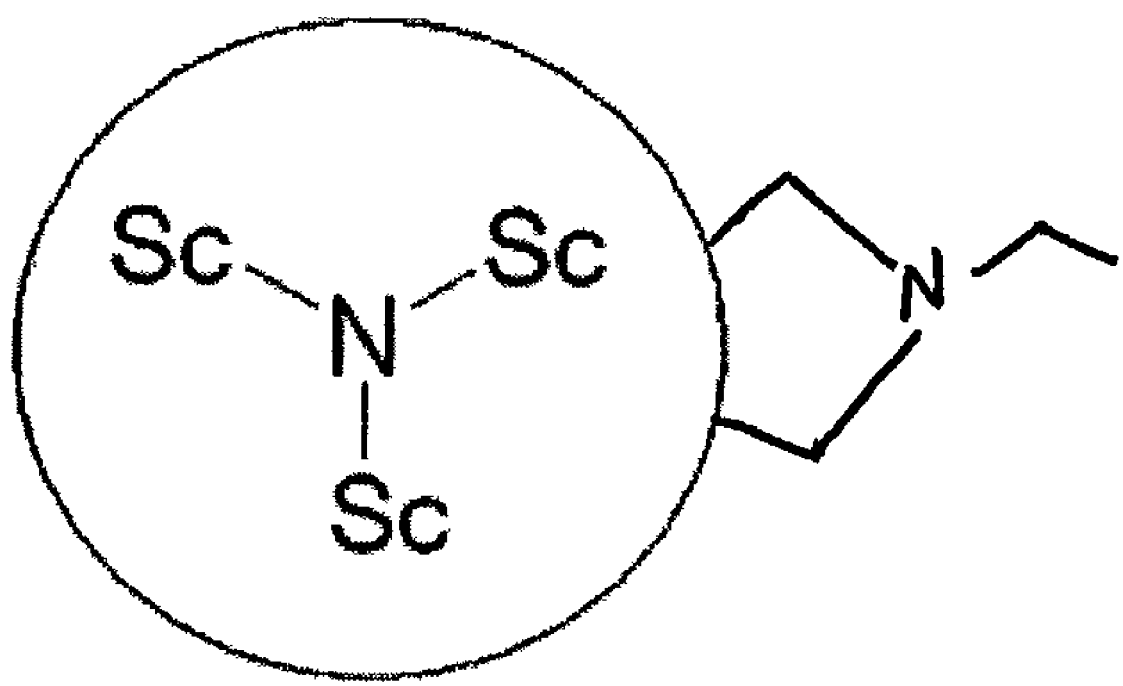
FIG. 4 illustrates the configuration of the metallofullerpyrrolidine $Sc_3N@C_{80}(C_4H_9N)$.

A 1,2,4-trichlorobenzene solution containing $Sc_3N@C_{80}$ (6.5 mg, 99%) was refluxed for 24 hours with an excess of 6,7-dimethoxyisochroman-3-one (99%, $^{13}C$ labelled) to achieve the $^{13}C$ labeled metallofullerene monoadduct. FIG. 3 illustrates the reaction scheme for the preparation of $Sc_3N@C_{80}(C_{10}H_{12}O_2)$. The reaction solution was dominated by a single reaction product and was purified by HPLC methods using a Trident-Tri-DNP column (Buckyclutcher column: Regis Chemical) with chloroform as the eluent. Matrix assisted (9-nitroanthracene20) laser desorption ionization time-of-flight mass spectrum (MALDI-TOF MS) showed a peak for the $^{13}C$ labeled monoadduct at m/z 1274 and a peak at m/z 1109 for the cleaved adduct. $^{13}C$ NMR showed a single narrow signal at 42.25 ppm for equivalent methylene carbons and suggests a plane of symmetry. The hydrogens attached to the methylene carbons are nonequivalent and centered at 3.41 and 3.57 ppm, respectively.

EXAMPLE 2

Preparation of $Sc_3N@C_{80}(C_4H_9N)$

An orthodichlorobenzene solution containing $Sc_3N@C_{80}$ (4.6 mg) was refluxed for 24 hours with an excess of N-ethylglycine (98%) and formaldehyde to achieve the metallofullerene monoadduct. The reaction solution was dominated by a single reaction The product and was purified by HPLC methods using a Trident-Tri-DNP column (Buckyclutcher column: Regis Chemical) with chloroform as the eluent. Matrix assisted (9-nitroanthracene20) laser desorption ionization time-of-flight mass spectrum (MALDI-TOF MS) showed a peak for the monoadduct at m/z 1180. FIG.

4 illustrates the configuration of a metallofullerpyrrolidine derivative $Sc_3N@C_{80}(C_4H_9N)$.

In accordance with the present invention trimetallic nitride endohedral metallofullerene derivatives having the general $A_{3-n}X_nN@C_m(R)$ are produced using the above described methods. This family of trimetallic nitride endohedral metallofullerene derivatives include unique molecules with extraordinary properties due to the wide variety of metals and metal clusters that can be encapsulated inside the carbon cages and the wide variety of groups that can be added to the exterior of the fullerene cage. By varying the groups on the exterior of the fullerene cage, one can fine tune the properties of the endohedral metallofullerene to a particular application. For example, these derivatives can have properties that can find utility in conductors, semiconductor, superconductors, or materials with tunable electronic properties such as quantum computers, optical limiters, nonlinear optical devices, ferroelectrics and dielectrics. Trimetallic nitride endohedral metallofullerenes derivatives having encapsulated radioactive metals, such as Ho, may be used for medical applications such as radioactive tracers, PET, MRI and X-ray contrast agents. These tracers may serve as fluorescent or optical tags. By varying the group on the exterior of the fullerene cage, the water solubility or bioactivity of the derivative may be varied. Further, trimetallic nitride endohedral metallofullerenes derivatives provide a new approach for surface dispersal for catalysts, coatings, and inks via a non-polar solvent (toluene, carbon disulfide, or 1,2-dichlorobenzene) or vacuum vaporization. The materials may be utilized directly as surface coatings or oxidized to the corresponding metal oxides.

It will therefore be readily understood by those persons skilled in the art that the present invention is susceptible to broad utility and application. Many embodiments and adaptations of the present invention other than those herein described, as well as many variations, modifications and equivalent arrangement, will be apparent from or reasonably suggested by the present invention and the foregoing description thereof, without departing from the substance or scope of the present invention.

Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims and the equivalents thereof.

What is claimed is:

1. An endohedral metallofullerene having the formula:

wherein:
A is a metal;
X is a second metal;
n is an integer from 0 to 3;
m is an even integer from about 68 to about 200; and
R is $C_4H_9N$ bonded to the $C_m$ fullerene cage through at least two carbon atoms on the $C_m$ fullerene cage.

2. The metallofullerene of claim 1 wherein m is 80.

3. The metallofullerene of claim 1 wherein:
A is selected from the group consisting of Scandium, Yttrium, Lanthanum, Gadolinium, Holmium, Erbium, Thulium, and Ytterbium; and
X is selected from the group consisting of Scandium, Yttrium, Lanthanum, Gadolinium, Holmium, Erbium, Thulium, and Ytterbium.

4. An endohedral metallofullerene having the formula:

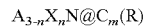

wherein:
A is a metal;
X is a second metal;
n is an integer from 0 to 3;
m is an even integer from about 68 to about 200; and
R is $C_{10}H_{12}O_2$ bonded to the $C_m$ fullerene cage through at least two carbon atoms on the $C_m$ fullerene cage.

5. The metallofullerene of claim 4 wherein m is 80.

6. The metallofullerene of claim 4 wherein:
A is selected from the group consisting of Scandium, Yttrium, Lanthanum, Gadolinium, Holmium, Erbium, Thulium, and Ytterbium; and
X is selected from the group consisting of Scandium, Yttrium, Lanthanum, Gadolinium, Holmium, Erbium, Thulium, and Ytterbium.

7. An endohedral metallofullerene having the formula:

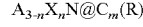

wherein:
A is a metal;
X is a second metal;
n is an integer from 0 to 3;
m is an even integer from about 68 to about 200; and
R comprises carbon and hydrogen, and wherein R forms a cyclic ring with at least two carbon atoms on the $C_m$ fullerene cage.

8. The metallofullerene of claim 7 wherein R forms a five-member ring on the $C_m$ fullerene cage.

9. The metallofullerene of claim 7 wherein R futher comprises an oxygen or nitrogen.

10. The metallofullerene of claim 7 wherein m is 80.

11. The metallofullerene of claim 7 wherein:
A is selected from the group consisting of Scandium, Yttrium, Lanthanum, Gadolinium, Holmium, Erbium, Thulium, and Ytterbium; and
X is selected from the group consisting of Scandium, Yttrium, Lanthanum, Gadolinium, Holmium, Erbium, Thulium, and Ytterbium.

12. The metallofullerene of claim 7 wherein X is Scandium.

13. The metallofullerene of claim 7 wherein X is Holmium.

14. The metallofullerene of claim 7 wherein X and A are different.

15. The metallofullerene of claim 7 wherein A is selected from the group consisting of a rare earth element and group IIIB element.

16. The metallofullerene of claim 15 wherein X is selected from the group consisting of a rare earth element and group IIIB element.

17. The metallofullerene of claim 7 wherein R forms a six-member ring with the $C_m$ fullerene cage.

18. The metallofullerene of claim 7 wherein A is Gadolinium.

19. The metallofullerene of claim 7 wherein R is bonded to the $C_m$ fullerene cage at a five-member ring and six-member ring junction of the $C_m$ fullerene cage.

20. The metallofullerene of claim 7 wherein $A_{3-n}X_nN@C_m(R)$ is a [4+2] cycloaddition product.

21. The metallofullerene of claim 7 wherein $A_{3-n}X_nN@C_m(R)$ is a [1, 3-dipolar] cycloaddition product.

22. The metallofullerene of claim 7 wherein $A_{3-n}X_nN@C_m(R)$ is a [2+1] cycloaddition product.

23. The metallofullerene of claim 7 wherein $A_{3-n}X_nN@C_m(R)$ is a [3+2] cycloaddition product.

24. The metallofullerene of claim 7 wherein $A_{3-n}X_nN@C_m(R)$ is a [2+2] cycloaddition product.

* * * * *